(12) United States Patent
Goetz et al.

(10) Patent No.: US 7,182,933 B2
(45) Date of Patent: Feb. 27, 2007

(54) TARGETING DRUG/GENE CARRIERS TO IRRADIATED TISSUE

(75) Inventors: Douglas J. Goetz, Athens, OH (US); Mohammad F. Kiani, Germantown, TN (US)

(73) Assignees: The University of Tennessee Research Corporation, Knoxville, TN (US); The Board of Trustess of Ohio University, Athens, OH (US)

( * ) Notice: Subject to any disclaimer, the term of this patent is extended or adjusted under 35 U.S.C. 154(b) by 693 days.

(21) Appl. No.: 09/975,899

(22) Filed: Oct. 12, 2001

(65) Prior Publication Data

US 2002/0044959 A1    Apr. 18, 2002

Related U.S. Application Data

(60) Provisional application No. 60/239,666, filed on Oct. 12, 2000.

(51) Int. Cl.
*A61K 49/00*   (2006.01)
*A61K 39/395*  (2006.01)
*A61K 9/27*    (2006.01)

(52) U.S. Cl. ............... 424/9.1; 424/130.1; 424/141.1; 424/450

(58) Field of Classification Search ............ 424/9.1, 424/450, 130.1, 141.1
See application file for complete search history.

(56) References Cited

U.S. PATENT DOCUMENTS 5,962,424 A    10/1999  Hallahan ............... 514/44
6,159,443 A  * 12/2000  Hallahan

FOREIGN PATENT DOCUMENTS

WO    WO 98/53852    * 12/1998

OTHER PUBLICATIONS

Mastrobattista et al.,Biochim. Biophys. Acta, 1999, 1419, 353-363.*
Patel et al., FASEB 1998, vol. 12 pp. 1447-1454).*

* cited by examiner

*Primary Examiner*—Christina Chan
*Assistant Examiner*—Michail A. Belyavskyi
(74) *Attorney, Agent, or Firm*—Benjamin Aaron Adler

(57) ABSTRACT

The present invention provides a biomolecular carrier of pharmaceuticals, comprising: a biomolecule carrier bearing molecules that bind to a cellular adhesion molecule expressed on endothelial cell; and a pharmaceutical. The present invention also provides a method of treating a pathophysiological state in an individual in need of such treatment, comprising the steps of: irradiating a target tissue or organ in said individual; and administering to said individual the biomolecular carrier disclosed herein.

1 Claim, 8 Drawing Sheets

HuEP

IgG

TARGETING DRUG/GENE CARRIERS TO IRRADIATED TISSUE

CROSS-REFERENCE TO RELATED APPLICATION

This application claims benefit of priority of provisional patent application U.S. Ser. No. 60/239,666, filed Oct. 12, 2000, now abandoned.

FEDERAL FUNDING LEGEND

This invention was produced in part using funds obtained through a grant from the National Institutes of Health. Consequently, the federal government has certain rights in this invention.

BACKGROUND OF THE INVENTION

1. Field of the Invention

The present invention relates generally to the fields of radiation and clinical oncology, radiotherapy, radioimmunobiology and nuclear medicine. More specifically, the present invention relates to a technique of targeting drug (or gene) carriers to select tissue via the up-regulation of adhesion molecules expressed on endothelial cells in response to exposure to radiation.

2. Description of the Related Art

Ionizing radiation (IR) is used widely to treat many conditions including cancer, arteriovenous malformations (AVM), macular degeneration, and intimal hyperplasia. Ionizing radiation therapy causes vascular lesions and damage in normal tissues. The microvasculature is quite sensitive to radiation (20) and is an important radiation dose-limiting factor in clinical applications. In almost all cases of therapeutic approach, the goal is to limit the exposure of normal tissue to the ionizing radiation while maximizing exposure to the diseased tissue. Indeed, improvement of techniques such as dose fractionation and conformal therapy (68), discovery of radioprotective drugs (78), and development of experimental methods of radiation therapy such as Microbeam Radiation Therapy (70) for reducing normal tissue toxicity of radiotherapy are currently active areas of research. In most cases, using modern clinical radiotherapeutic techniques, radiation damage can be limited to a core of diseased tissue and the immediate normal tissue surrounding it.

Ionizing radiation damage to the microcirculation is manifested in many forms including increased capillary permeability and up-regulation of inflammatory processes. An increase in permeability is an early and universal response of the microvasculature to ionizing radiation (19;46;50;51;75). For example, there is an increase in the blood-brain-barrier permeability in response to irradiation (22;62). Although this can lead to extravasation of blood proteins which may exacerbate tissue injury, the increased permeability can enhance delivery of chemotheraputic drugs across the blood-brain-barrier (61;62;64). Therefore, targeted drug delivery to irradiated tissue will not only provide a means to selectively deliver the drug but will also deliver the drug to a site of increased vascular permeability.

It has been known for over 15 years that exposure of normal and diseased tissue to irradiation causes an increase in leukocyte infiltration of the tissues (1;8;44;53;65;76). A key component of this process is the adhesion of leukocytes to the microvascular endothelium. A variety of studies focused on elucidating a detailed understanding of leukocyte adhesion in general (i.e. in response to stimuli other than radiation) have revealed that the movement of leukocytes from within the vasculature to the extravascular space involves a well orchestrated set of adhesion events (10;43; 49;72). This adhesion cascade is mediated in part by adhesive bonds which form between glycoproteins (ligands) present on the leukocytes and cognate glycoproteins (receptors) present on the endothelium.

A key paradigm in this adhesion cascade is that certain endothelial cell adhesion molecules are inducible. That is, they are expressed at a low level, if at all, on endothelium within normal tissue, but dramatically up-regulated in response to appropriate biochemical stimuli (e.g. cytokines such as IL-1β) (10). Thus, in response to various cytokines, the endothelium becomes activated and increases its expression of receptors that bind ligands on the leukocytes. These receptors include E-selectin (CD62E), P-selectin (CD62P), VCAM-1 (CD54) and ICAM-1 (CD106).

Leukocytes attach to the endothelium, for the most part via the selectins, and begin to translate along the vessel wall (roll) at a velocity which is significantly lower than leukocytes in the free stream (72). As the leukocytes roll, they become activated in response to chemokines (18;72). The activation involves a number of changes to the leukocytes including an alteration in the density of the integrins on the leukocyte surface as well as an increase in the "stickiness" (a conformational change) of the integrins for their cognate endothelial cell adhesion molecules (e.g. ICAM-1) (15;56). The leukocytes firmly adhere to the endothelium via the integrins and proceed to migrate between adjacent endothelial cells into the extravascular space in part via PECAM-1 (CD31).

As noted above, a key component of leukocyte emigration is endothelial cell activation wherein the adhesion molecule profile on the lumenal surface of the endothelium is altered. Recognition of these drastically different endothelial surfaces has lead to the concept of endothelial cell adhesion molecule mediated targeted drug delivery (3;4;6;7;16;71). In this therapeutic approach, a drug would be incorporated into a carrier (e.g. a liposome (3;4;7;71) or a biodegradable particle (16;28)). The carrier would have a ligand for an endothelial cell adhesion molecule (e.g. E-selectin) that is selectively expressed on the target endothelial segment. Ideally the carrier would bind to the target endothelial segment (e.g. endothelium within a site of inflammation) via the selectively expressed receptor and not bind to non-target endothelium.

It is reasonable to anticipate that some of the molecular mechanisms involved in inflammatory processes initiated by insults other than radiation will also be operative in radiation induced inflammation. Recent literature suggests that this is, at least in part, true. In vitro studies aimed at characterizing the response of endothelial cells to irradiation have consistently shown ICAM-1 up-regulation on endothelial cells derived from large vessels (21;32;73) and vessels of the microvasculature (2;41). In vivo studies have also found up-regulation of ICAM-1 (12;35;36;42;47;53;58) and have ascribed increased leukocyte adhesion to the endothelium to an up-regulation of ICAM-1 (53;59). Indeed, radiation induced inflammatory response is significantly attenuated in mice deficient in ICAM-1 relative to wild type mice (35). In a recent clinical study (39) a significant increase in ICAM-1 expression in head and neck cancer patients treated with fractionated radiotherapy (30–60 Gy in 2 Gy daily fractions) has been reported.

At present the expression of E-selectin in response to radiation remains controversial. The expression of E-selectin has been studied in vitro using endothelial cells derived from large veins (i.e. HUVEC). One group reported significant up-regulation of E-selectin on human umbilical vein endothelial cells (31–33). In addition, this group found that the irradiated human umbilical vein endothelial cells supported E-selectin dependent adhesion of a leukocytic cell line (HL-60 cells) in semi-static adhesion assays (33). In contrast, others have found that E-selectin is not up-regulated on human umbilical vein endothelial cells in response to radiation (60; 21). It has also been found that irradiated human umbilical vein endothelial cells do not support the adhesion of HL-60 cells under in vitro flow conditions designed to mimic conditions present in vivo. Specifically, no adhesion of HL-60 cells were observed at shear stresses between 0.5–2.0 dynes/cm$^2$ on post-IR human umbilical vein endothelial cells. Note that the lowest physiologically relevant in vitro shear stress is thought to be 0.5 dyne/cm$^2$ (26). In contrast to the data on endothelial cells derived from large vein (i.e. human umbilical vein endothelial cells), a modest up-regulation of E-selectin on dermal microvascular endothelial cells (i.e. HDMEC) was observed which is in agreement with Heckman et al. (41). Consistent with this finding, in vitro flow adhesion assays revealed that post-IR dermal microvascular endothelial cells did support a small increase in HL-60 cell adhesion at relatively low (<=1.5 dynes/cm$^2$) fluid shear. In vivo, it has been observed that there is an increase in the number of leukocytes which roll along the vessel wall in response to radiation (1;53;59). Consistent with this finding, E-selectin has been found within the microvasculature of the lung in response to radiation (36). A significant increase in E-selectin expression in head and neck cancer patients treated with fractionated radiotherapy (30–60 Gy in 2 Gy daily fractions) has also been reported (39).

A few studies have probed for the presence of VCAM-1 in response to radiation in vitro. VCAM-1 was observed to be up-regulated in irradiated skin microvascular endothelium (41) but not irradiated human umbilical vein endothelial cells (21;32). VCAM-1 was not up-regulated in head and neck cancer patients undergoing radiotherapy (39).

The expression of P-selectin post-IR has also been probed. One report found that P-selectin is localized to the vascular lumen of several irradiated tumors in vivo and increases in a time dependent manner until 24 hours post-IR (34). P-selectin is also reportedly translocated to the cell membrane in human umbilical vein endothelial cells within 30 minutes post-IR in vitro and in vivo. It is accumulated in the lumen of irradiated blood vessels in the lung and intestine but not in the brain or kidney (30;34;37).

Surface protein and mRNA levels of PECAM-1 (CD31), which is involved in the adhesion and transendothelial migration of leukocytes, has been shown to be up-regulated after irradiation in both human umbilical vein endothelial cells and tissue specimens from radiotherapy patients (63) but not in HDMEC (41). The up-regulation of PECAM-1 was found to be accompanied with increased transendothelial migration of leukocytes post-IR and this increased migration was inhibited with a mAb to PECAM-1 (63).

Although the issue of which endothelial cell adhesion molecules are expressed in response to radiation remains controversial, it is abundantly clear that the endothelial cell adhesion molecule profile is significantly altered in response to radiation. There is very convincing evidence that ICAM-1 and PECAM-1 are up-regulated. Although less clear, there is a modest amount of data suggesting that E-selectin is up-regulated as well. Even more noteworthy is that both ICAM-1 and E-selectin were significantly up-regulated in oral mucosa of head and neck cancer patients treated with radiotherapy (30–60 Gy in 2 Gy daily fractions) (39). The radiation induced up-regulation of endothelial cell adhesion molecules provides the opportunity to target drugs to select tissue via a combination of radiation and ligand-receptor drug targeting technology.

To clarify how the radiation therapy-targeted drug delivery scheme might work, consider the treatment of cancer as an example. Cancer patients are often treated with radiotherapy, chemotherapy or a combination of both. In an effort to limit side effects, the radiotherapy is designed to maximize radiation exposure to the cancerous tissue while minimizing exposure to normal tissue. Similarly, it would be ideal for a chemotherapeutic agent or a gene to be delivered only to the cancerous tissue and not to healthy tissue. Indeed, achieving this goal is the focus of a variety of drug delivery research.

In the combination radiation/targeting therapeutic model, a ligand-bearing drug carrier would be administered subsequent to, or in conjunction with, the radiotherapy. A variety of materials could be used for the drug carrier including liposomes or carriers made from biodegradable polymers. The drug carrier would contain a therapeutic agent (e.g. an organic compound, or a nucleic acid) and, on its outer surface, a recognition molecule (ligand) for a cognate molecule (receptor) that is expressed selectively (due to exposure to the radiation) on the lumenal surface of the endothelium within the irradiated tissue. Ideally, these carriers would bind predominately within the vasculature of the irradiated tissue (i.e. the cancerous tissue) and not bind to the vasculature of normal tissue. In this manner, the radiation induced up-regulation of a endothelial cell adhesion molecule(s) within the diseased tissue is used as a target to deliver therapeutic agents (drugs, genes, etc.) selectively to the site of disease.

The prior art is deficient in the ability to target drug (or gene) carriers to select tissue via the up-regulation of adhesion molecules expressed on endothelial cells in response to exposure to radiation. The present invention fulfills this long-standing need and desire in the art.

SUMMARY OF THE INVENTION

Radiotherapy is used to treat a variety of diseases. It is well established that the microvasculature of tissue exposed to ionizing radiation is significantly altered. These changes include an up-regulation of certain adhesion molecules on the lumenal surface of the endothelium. The radiation induced up-regulated expression of endothelial adhesion molecules provides an avenue for targeting drugs to select tissues. Please see FIG. 1 for a schematic of this approach.

It is an object of the present invention to develop drug carriers which bear ligands to adhesion molecules expressed on irradiated endothelial cells. The carriers are made of polystyrene (model carriers), as well as biodegradable polymers.

It is another object of the present invention to quantify the extent of selective and specific adhesion/deposition of drug carriers on irradiated endothelial cells under in vitro flow conditions that simulate flow conditions present in vivo.

It is another object of the present invention to demonstrate this targeted delivery technology in vivo in a mouse closed cranial window model.

In one embodiment of the present invention, there is provided a biomolecular carrier of pharmaceuticals, comprising: a biomolecule carrier bearing molecules that bind to a cellular adhesion molecule expressed on endothelial cell; and a pharmaceutical.

In another embodiment of the present invention, there is provided a method of treating a pathophysiological state in an individual in need of such treatment, comprising the steps of: irradiating a target tissue or organ in said individual; and administering to said individual the biomolecular carrier described herein.

Other and further aspects, features, and advantages of the present invention will be apparent from the following description of the embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate embodiments of the invention and therefore are not to be considered limiting in their scope.

DETAILED DESCRIPTION OF THE INVENTION

Figure 1:
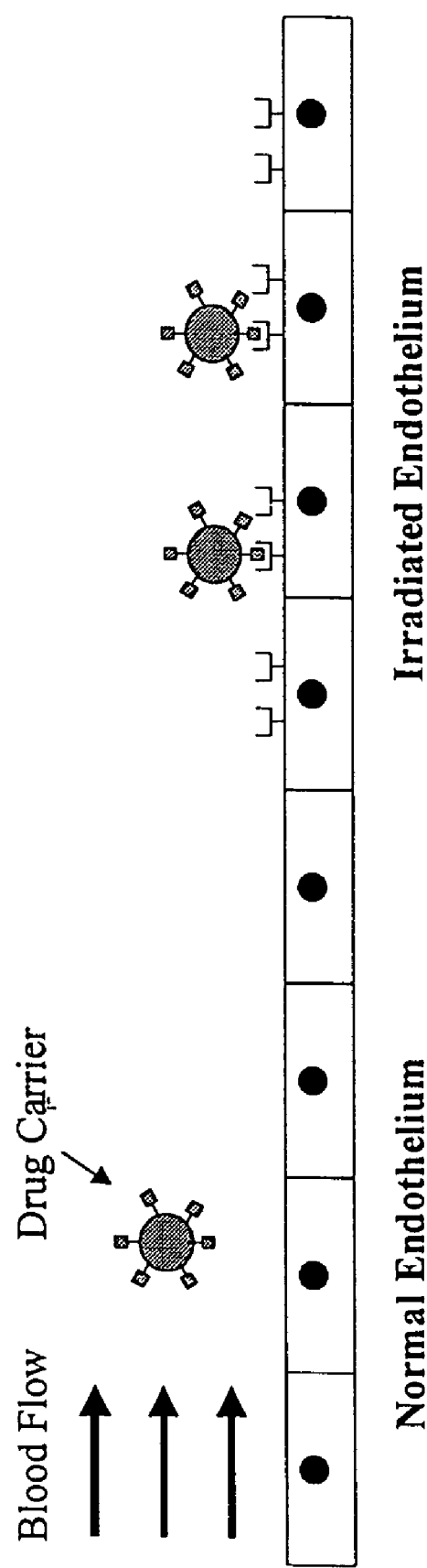
FIG. 1 shows a schematic of the proposed targeted drug delivery scheme.

The present invention demonstrates development of a drug delivery scheme to selectively target drug/gene carriers to tissue that has been irradiated for therapeutic purposes. Radiation therapy is used to treat many conditions including cancer, arteriovenous malformations (AVM), macular degeneration, and intimal hyperplasia. It is well established that the microvasculature of tissue exposed to ionizing radiation is significantly altered. These changes include an up-regulation of certain adhesion molecules on the lumenal surface of the endothelium. The radiation induced up-regulated expression of endothelial adhesion molecules provides a potential avenue for targeting drugs and/or genes to select tissues. There have been very few, if any, studies exploring this potentially powerful therapeutic approach.

The targeted drug delivery technique of the present invention has applications in the treatment of cancer, restenosis and several other diseases. This drug delivery technique is developed in vitro using cultured human endothelial cells and in vivo in the mouse cranial window model. Cultured human endothelial cells and human blood provides the needed information to develop and optimize this technique.

These studies utilize C57BLK mice for in vivo experiments involving the cranial window preparation (selected as a relatively inexpensive mammalian species in order to model targeted drug delivery to irradiated tissue). Investigations concerning targeted drug delivery are conducted in an animal system since physiological changes and the resultant effects on the microvasculature are investigated in vivo to establish baseline data for the modeling studies. Approximately 20 mice/month are purchased and housed for an average of 30 days. These mice are housed 2 per cage under 12 hr light/dark cycles with food and water ad libitum. Adult C57BLK mice are anesthetized with an i.m. injection of 87 mg of ketamine/kg and 13 mg of xylazine/kg. The body temperature is maintained between 36 and 37° C. The cranial window is prepared for observation under an intravital microscope as discussed herein The mice are euthanised by an overdose of KCI. Single or fractionated doses of (2–40 Gy) irradiation (Siemens MD-2 linear accelerator (6 mV X-rays) located at the St. Jude Children's Research Hospital) are utilized to study targeted drug delivery the irradiated tissue. Protocols typically involve observation of the microvasculature 1–30 days after single or fractionated doses of ionizing radiation. The mice are anesthetized throughout the surgical procedure and data collection. Radiation is delivered locally to one hemisphere of the brain and the rest of the body is shielded.

The present invention shows the feasibility of targeting drug carriers to select tissue via the up-regulation of adhesion molecules expressed on endothelial cells in response to exposure to radiation. More specifically, it is a specific object of the present invention to (1) develop drug carriers which bear ligands to adhesion molecules expressed on irradiated endothelial cells, (2) quantify the extent of selective and specific adhesion/deposition of drug carriers on irradiated endothelial cells under in vitro flow conditions that simulate flow conditions present in vivo, and (3) demonstrate the feasibility of this targeted delivery technology in vivo in a mouse closed cranial window model. The present invention provides proof that this therapeutic approach is feasible and one can test this approach in a diseased system (e.g. tumor) in vivo.

The present invention is directed to a biomolecular carrier of pharmaceuticals, comprising: a biomolecule carrier bearing molecules that bind to a cellular adhesion molecule expressed on endothelial cell; and a pharmaceutical. Representative examples of substances which may be used for the carrier include biodegradable particles, liposomes, microbubbles, polymersomes and synthetic secretory granules. Representative examples of targeting molecules that can be put on the carrier include intact antibody or antibody fragments such as Fab, Fv, $F(ab')_2$, and sFv that bind to cellular adhesion molecule as well as ligands that bind to cellular adhesion molecule. Representative examples of cellular adhesion molecule include ICAM-1, E-selectin, P-selectin, and VCAM-1. Preferably, in the case of cancer the pharmaceutical is an anti-neoplastic compound but in other diseases commonly treated with radiotherapy numerous other pharmaceuticals could be used in this technique.

The present invention is also directed to a method of treating a pathophysiological state in an individual in need of such treatment, comprising the steps of: irradiating a target tissue or organ in said individual; and administering to said individual the biomolecular carrier disclosed herein. Preferably, the biomolecular carrier of pharmaceuticals, comprises: a biomolecule carrier bearing molecules that bind to a cellular adhesion molecule expressed on endothelial cell; and a pharmaceutical. Representative examples of substances which may be used for the carrier include biodegradable particles, liposomes, microbubbles, polymersomes and synthetic secretory granules. Representative examples of targeting molecules that can be put on the carrier include intact antibody or antibody fragments such as Fab, Fv, $F(ab')_2$, and sFv that bind to cellular adhesion molecule as well as ligands that bind to cellular adhesion molecule. Representative examples of cellular adhesion molecule include ICAM-1, E-selectin, P-selectin, VCAM-1. Preferably, the pharmaceutical is an anti-neoplastic compound. Numerous other pharmaceuticals could also be used in this method. This technique may be used to treat a wide variety of pathophysiological states including cancer, arteriovenous malformations (AVM), macular degeneration and restenosis.

The following examples are given for the purpose of illustrating various embodiments of the invention and are not meant to limit the present invention in any fashion. In FIGS. 2, 3, 5, 7, 8 and 11, significant difference from appropriate controls is indicated by * ($p<0.05$) or ** ($P<0.01$) as determined from one way analysis of variance (ANOVA) and a multiple comparison method (Fisher's least significant difference, LSD) to discriminate between the means. Data are presented as Mean±SEM.

EXAMPLE 1

Generation of Ligand-Coated Polystyrene Particles

Due to their ease of use, polystyrene particles were used first. The polystyrene particles were purchased from Bangs Laboratories (Fishers, Ind.). The particles were available in a variety of diameters (20 nm–10 μm) and with various incorporated fluorescent dyes. Since particles in the nanometer range cannot be detected by bright field light, fluorescent nanospheres were used and the fluorescent label was used to detect the nanospheres on a cellular surface.

The ligand coated polystyrene particles were prepared as follows. The particles were coated with protein A via passive adsorption. To achieve this, the particles were incubated in a 0.1 M NaHCO3, pH 9.2 buffer containing 300 μg/ml protein A at room temperature for over an hour. Following the adsorption, the particles are washed, incubated in a blocking buffer (Hank's balanced saline solution supplemented with 1% human or rat serum albumin), washed and incubated with a specific monoclonal antibody to an endothelial cell adhesion molecule diluted in blocking buffer. After a 1 hour incubation, the monoclonal antibody coated particles are washed and stored in the blocking buffer prior to use in an assay.

Particles coated with a monoclonal antibody to ICAM-1 (commercially available through companies such as R&D Systems; Minneapolis, Minn.) are initially generated. As the studies progress, monoclonal antibodies to other endothelial cell adhesion molecules (e.g. E-selectin) are used. The final surface density of the monoclonal antibody on the particles can be controlled by altering the amount of monoclonal antibody used in the monoclonal antibody coating step. The surface density of monoclonal antibodies on the particles is quantified via radiolabelling assays as described (69). When working with microspheres, the washing steps (separation of the particles from solutions) are achieved via centrifugation and the concentration of microspheres in a solution is determined via a hemocytometer. When working with nanospheres, the separations are achieved via gel filtration and the concentration of nanospheres in a solution will be determined via absorbance readings and comparison to a standard curve as described (6). These methods are well established (25) and allow generatation of ligand coated particles.

EXAMPLE 2

Generation of Ligand-Coated Biodegradable Particles

Although the polystyrene particles are well suited for some studies, polystyrene is not a very relevant drug delivery carrier. A more physiologically relevant drug delivery carrier would be made of a variety of materials including biodegradable polymers.

Recently much attention has been given to the use of particles made from biodegradable polymers as attractive drug carriers (5;16;28). Routine particles made from biodegradable polymers have two drawbacks. First they are rapidly removed from the circulation and second they apparently adsorb a low level of ligand (16). Dr. Shakesheff (University of Nottingham, Nottingham, UK) has generated a biotinylated PEGylated co-polymer that appears to circumvent these problems.

Avidin chemistry is used to couple mAbs to particles made from this polymer (9). Microspheres from the biotinylated PEGylated co-polymer are made as these particles are easy to detect with bright field microscopy. Monoclonal antibodies are coupled to the co-polymer microspheres by first coupling avidin to the biotin covalently linked to the polymer. After this step, the microspheres are washed and incubated in a solution containing a biotinylated monoclonal antibody to an endothelial cell adhesion molecule (e.g. anti-ICAM-1). After this step, the microspheres are washed and held in blocking buffer until used in an assay. The success of the coupling procedure is shown via adhesion assays as described herein. Then, ligand coated biodegradable nanospheres are generated. Due to their small size, it is impossible to visualize the nanospheres with bright field microscopy. Thus a fluorescent tag is incorporated into the nanoparticles to allow their detection using fluorescently labeled avidin during the coupling procedure.

EXAMPLE 3

Testing the Adhesion of the Ligand Coated Particles to Their Cognate Adhesion Molecules In Vitro After coupling the mAbs to the microspheres, in vitro adhesion assays are used to determine if the particles exhibit selective adhesion to cognate presenting cellular monolayers. Static adhesion assays are employed as a large number of conditions can be tested in a single assay. The goal here is simply to determine if the ligand is coupled to the particles in such a way that the ligand is able to support adhesion to its cognate receptor. Systematic detailed studies are conducted of the interaction of the particles with the cognate receptor presenting surfaces under in vitro fluid dynamic conditions that mimic, in part, conditions present in vivo. Adhesive substrates are prepared in wells of 96 well plates. The adhesive substrates consist of human umbilical vein endothelial cells (HUVEC) treated with IL-1β 4 hours prior to the adhesion assays to elicit expression of inducible adhesion molecules (e.g. ICAM-1 on activated human umbilical vein endothelial cells), unactivated human umbilical vein endothelial cells (negative control for activated HUVEC), tissue culture plastic coated with a recombinant purified form of a particular endothelial cell adhesion molecule (e.g. ICAM-1) or tissue culture plastic coated with blocking proteins (e.g. human serum albumin as negative control for tissue culture plastic coated with adhesion molecules). The ligand coated particles are added to the wells of the 96 well plates. After a set time of incubation, the wells are washed and the number of particles remaining in each well determined. For the microspheres this is determined by counting the number of particles present under bright field microscopy. For the nanospheres this involves recording various fields of view under fluorescent illumination and then analyzing the intensity via image analysis. In certain wells, particles coated with a control protein (e.g. human serum albumin) is added rather than the ligand coated particles. In certain wells, the adhesive substrates are pre-treated with fluid phase monoclonal antibodies prior to the introduction of the particles.

Testing the adhesion of the particles under the above listed conditions allows determination of whether the ligand coated particles exhibit specific selective adhesion to substrates expressing the cognate endothelial cell adhesion molecule. For example, anti-ICAM-1 coated particles should show high levels of binding to activated human umbilical vein endothelial cells relative to unactivated human umbilical vein endothelial cells and this adhesion should be inhibited by pre-treatment of the human umbilical vein endothelial cells monolayers with fluid phase anti-ICAM-1 but not pre-treatment with monoclonal antibody W6/32 which recognizes Class I. In addition, anti-ICAM-1 coated particles should bind to tissue culture plastic coated with ICAM-1 to a much greater extent than they bind to tissue culture plastic coated with human serum albumin.

Analysis of variance (ANOVA) are used to test for statistical significance of any observed differences; a multiple comparison procedure (Fisher's least significant difference, LSD) will be used to discriminate among the means. Differences are considered statistically significant if P<0.05.

Biodegradable particles are only one kind of drug carrier that could be used. Other classes of carriers include liposomes (55), microbubbles (74), polymersomes (17) or synthetic secretory granules (45).

EXAMPLE 4

Endothelial Cell Culture

Microspheres and nanospheres bearing mAbs to ICAM-1 are used since ICAM-1 is up-regulated by ionizing radiation. Other adhesion molecules, e.g. E-selectin, may also be used.

Human umbilical vein endothelial cells (HUVEC) and human dermal microvascular endothelial cells (HDMEC) are purchased from Colonetics, Inc. Human umbilical vein endothelial cells are maintained in M199 supplemented with FBS, L-glutamine, heparin, endothelial growth factor and penicillin/streptomycin on gelatin coated tissue culture plastic. Confluent cells are trypsinized and subcultured at a ratio of 1:3. All studies are conducted on passage 3–6 of these cells. HDMEC are maintained in MCDB131 media supplemented with human serum, FBS, L-glutamine, cyclic AMP, hydrocortisone acetate and penicillin/streptomycin. The cells are grown on 0.2% gelatin coated tissue culture dishes. Confluent cells are trypsinized and subcultured at a ratio of 1:3. All studies are conducted on passage 3–5 of these cells. For the assays described below, the endothelial cells are grown in 35 mm$^2$ tissue culture dishes.

EXAMPLE 5

Irradiation and Flow Cytometry

Prior to irradiation, confluent endothelial cells are replenished with fresh media. HDMEC media are replaced with media lacking cyclic AMP which has been found to suppress the expression of E-selectin (26). Cells are irradiated with single doses of 10, 5, or 2 Gy or fractionated doses of 20–30 Gy (3 Gy per day) ionizing radiation at a dose rate of 4.2 Gy per minute. Cells taken to the radiation facility but not irradiated are used as controls. IL-1β (10 U/ml) activated cells serve as positive controls. Up-regulation of adhesion molecules on irradiated endothelial cells is probed using flow cytometry. Adhesion assays are conducted with cells 5 hr, 24 hr, 48 hr and 72 hr post irradiation.

Presence of various adhesion molecules on irradiated endothelial cells is probed via flow cytometry. At the respective time points post-IR (5 hr, 24 hr, 48 hr and 72 hr), endothelial cells are harvested from the tissue culture dish with 0.01% EDTA-trypsin mixture in the presence of 1% BSA, washed in phosphate buffer saline and incubated (30 minutes at 4° C.) with appropriate mAbs to endothelial cell adhesion molecules (e.g. monoclonal antibody to ICAM-1). Following the incubation, the endothelial cells are washed and incubated with secondary antibody (goat F(ab')$_2$, FITC conjugated anti-mouse IgG, heavy and light Chain specific) for 30 minutes at 4° C. Following the incubation, the cells are washed, fixed in 2% formaldehyde and analyzed by flow cytometry. Harvested endothelial cells treated with isotype non-specific murine IgG and not treated with a primary mAb serve as negative controls. Endothelial cells pre-treated with IL-1β 4 hr. prior to the assays will serve as positive controls.

EXAMPLE 6

Quantify the Extent of Selective and Specific Adhesion/Deposition of the Carriers on Irradiated Endothelial Cells A parallel plate flow chamber is used to study the interaction of the ligand coated particles with various adhesive substrates (14). The flow chamber has an inlet for the entry of the drug carriers which are suspended in endothelial cell growth media and an outlet connected to a syringe pump which controls the flow rate. A second outlet is connected to a vacuum pump to seal the flow chamber and the 35 mm tissue culture dish containing the adhesive substrate The height and width of the flow chamber, the viscosity of the media and the volumetric flow rate determine the wall shear stress in the flow chamber. Once the flow chamber is sealed, it is transferred to the stage of an inverted phase contrast microscope. The microscope has an attached video camera which is connected to a VCR and monitor. Once on the microscope stage, the adhesive substrate is rinsed and the flow of the particle suspension initiated. The particles are coated with either a ligand for an endothelial cell adhesion molecule or non-specific IgG (negative control). After a certain amount of time, the images of several fields of view are recorded for later off-line analysis. When microspheres are in use, the images are taken under bright field light microscopy and the number of microspheres present determined by simply counting the number of microspheres observed. When nanospheres are used, the images are recorded under fluorescent illumination. The images are imported into an image analysis work-station and the fluorescent intensity of the fields of view determined to gain a semi-quantitative measure of the number of nanospheres present on the adhesive substrate.

The adhesive substrates consist of human umbilical vein endothelial cells and HDMEC. In certain assays these endothelial cells are treated with radiation a set amount of time prior to the adhesion assay. Negative control monolayers are prepared in exactly the same manner although they will not be treated with radiation. Positive control monolayers are treated with IL-1β 4 hours prior to the adhesion assay to elicit expression of cytokine inducible endothelial cell adhesion molecules. In certain assays the endothelial cells are treated with fluid phase monoclonal antibodies prior to the introduction of the particles. Several parameters are varied to gain insight into the effect of these parameters on the selective adhesion. These parameters include the shear, the particle size, the ligand density and the ligand used to target a given endothelial cell adhesion molecule and the endothelial cell adhesion molecule targeted. Since the nanoparticles may be endocytosed by the endothelial cells, certain assays are conducted at reduced temperature (4° C.) to gain insight into the role of endocytosis in the accumulation of the particles on/within the endothelial cells.

Testing the adhesion of the particles under the above listed conditions allows determination of whether the ligand coated particles exhibit specific-selective adhesion to post-irradiation endothelial cells relative to non-irradiated treated endothelial cells. For example, if anti-ICAM-1 coated biodegradable nanospheres exhibit much greater levels of binding to post-IR human umbilical vein endothelial cells relative to non-irradiated human umbilical vein endothelial cells and this augmented adhesion is inhibited by pre-treatment of the post-irradiated human umbilical vein endothelial cells with fluid phase anti-ICAM-1 but not pre-treatment with mAb W6/32 which recognizes Class I, the data would indicate that the anti-ICAM-1 biodegradable nanospheres exhibit specific-selective adhesion to post-irradiated human umbilical vein endothelial cells.

By determining the ratio of the binding to post-IR human umbilical vein endothelial cells relative to non-IR human umbilical vein endothelial cells, insight into the selectivity of the adhesion can be gained. By systematically altering the biophysical parameters (e.g. ligand density, shear, targeting ligand) and determining the resulting affect on selectivity one gains insight into what role these various parameters can have on the selective adhesion. Note that the deposition of the particles on the surface of the endothelial cells is a function of several interrelated processes (e.g. transport and adhesion). Thus, to rationally interpret this data, one can use theoretical models that relate observed adhesion/deposition to adhesive mechanics (11;38) and transport (48).

EXAMPLE 7

Targeted Delivery Technology In Vivo in a Mouse Closed Cranial Window Model

The mouse cranial window model is used as a model of normal tissue because the brain is a clinically relevant tissue in radiotherapy and pial vessels can be studied in an animal survival model using intravital microscopy techniques. Either left or right hemisphere of mice are locally irradiated at 7–8 weeks of age and in each animal the unirradiated hemisphere are used as control. As an additional control, the interaction of the carriers with endothelium in each microvessel is measured before and after irradiation.

Prior to surgery animals are anesthetized with an i.m. injection of 15 μL of Ketaset (87 mg ketamine/mL+13 mg Xylazine/mL). Body temperature is maintained at approximately 37° C. by convective heating. Animals are placed on a small animal stereotaxic frame. All surgical procedures are carried out under aseptic conditions. The animal is prepped with three applications of iodine to the shaved scalp before the initial incision is made. The scalp and tissue from a 1.5×1.5 cm area bilaterally over the parietal cortex is removed. Bleeding from soft tissue is controlled via heat cauterization as needed and the underlying fascia is blunt dissected. A circular cranial window extending from the coronal to the lambdoid sutures centered on the sagittal suture is traced using a dental drill at low speed. Care is taken to avoid frictional heat created by drilling for extended periods in any one area. Once the window has been sufficiently drilled out, the flap of bone in gently removed with forceps and the underlying tissue washed with repeated applications of sterile artificial cerebrospinal fluid (ACSF). Slight bleeding from bridging vessels is allowed to clot without intervention. From this point on, all manipulations to the brain are carried out under a layer of sterile artificial cerebrospinal fluid. The dura is punctured with a 30 gauge needle and the tissue excised with microdissecting scissors, with great care taken not to make contact with the underlying brain tissue. Superficial bleeding is allowed to stop without intervention and the tissue is irrigated regularly with sterile artificial cerebrospinal fluid. A quartz plate resting on the bone surrounding the cranial window is glued to the surrounding bone using cyanocrylate glue. After recovery from anesthesia windowed animals are returned to the animal facilities and are given one week to recover from surgery.

EXAMPLE 8

Animal Irradiation

C57-black mice at 7–8 weeks of age (around 25 g) are irradiated. Prior to irradiation animals are sedated with an i.m. injection of a mixture of 87 mg/kg ketamine and 13 mg/kg xylazine. A local single dose (5, 10, 20 Gy) or fractionated doses (20–40 Gy in 2 Gy daily fractions) of radiation is delivered to randomly chosen left or right hemisphere of the brain at a rate of 2 Gy/min using a Siemens MD-2 linear accelerator (6 mV X-rays). A collimator 1.0 cm in diameter and normally used for human stereotactic radiosurgery is used to localize the radiation dose to the left or the right brain. Tissue equivalent bolus is placed above and below the head to establish electronic equilibrium and to insure the prescribed dose is delivered uniformly to the brain.

EXAMPLE 9

Intravital Microscopy Data Collection

Intravital microscopy techniques are used to compare the interaction of model fluorescent drug carriers and biodegradable drug carriers with endothelial cells in postcapillary venules in the irradiated brain hemisphere of each animal with the unirradiated (control) hemisphere of the same animal (n=6–7 mice per group). These postcapillary venules are generally the site of up-regulation of adhesion molecules in response to irradiation and are usually in the range of 15–50 μm in diameter. The drug carriers are injected via tail vain. All experiments are performed on a Nikon Measurescope MM-11 intravital microscope. Venule diameters are observed and recorded under reflected light illumination using a custom-designed epi-illumination filter cube (cross polarized excitation and emission filters along with a band pass 550±20 nm excitation filter) with a 100 W mercury lamp. Images are observed with a CCD camera in conjunction with an intensifier. Experiments are recorded on SVHS tape and analyzed offline using a computerized video imaging system.

EXAMPLE 10

Control Experiments

A series of control experiments are performed to ascertain the preferential adhesion of antibody coated microspheres to irradiated tissue. In one group of animals (n=6) the brain is locally irradiated (20 Gy local dose) and adhesion of microspheres to the microvasculature of non-irradiated tissue such as the cremaster, mesentery, liver and lung is compared to that of the brain using well-established intravital microscopy techniques (29;57;66). In another group of animals (n=6) the cremaster muscle (testicle areas) is locally irradiated (20 Gy local dose) and adhesion of microspheres to the microvasculature of non-irradiated tissue such as the brain, mesentery, liver and lung is compared to that of the cremaster. In these experiments antibody bearing particles are injected directly in to arteries upstream of the irradiated tissue (carotid artery for the brain and iliac artery for the cremaster).

Nanospheres bearing antibodies to ICAM-1 are used. E-selectin and other adhesion molecules can also be used. Initially, 2 μm red and blue fluorescent polystyrene (model carriers) microspheres which bear ligands to adhesion molecules expressed on irradiated endothelial cells or human IgG (as control) are used. The number of these microspheres interacting with the microvascular endothelium of irradiated tissue can be easily quantified by using dual filter fluorescent microscopy. By switching between red and blue fluorescent filter cubes the number of microspheres which bear ligands to adhesion molecules expressed on irradiated endothelial cells vs. control can be quantified. After verifying the enhanced interaction of fluorescent microspheres bearing ligands to adhesion molecules on their surface with irradiated tissue, biodegradable drug carriers are then used to selectively target irradiated endothelial cells. Fluorescent optical techniques as described above are used to quantify enhanced interaction of these drug carriers with irradiated tissue microvasculature.

EXAMPLE 11

Up-Regulation of Adhesion Molecules on Irradiated Endothelial Cells In Vitro

The expression of E-selectin and ICAM-1 on human umbilical vein endothelial cells (HUVEC), human microvascular endothelial cells (HDMEC) and transformed microvascular endothelial cells (HMEC-1) was investigated at 5 hr, 24 hr, 48 hr and 72 hr post-irradiation. Both E-selectin and ICAM-1 have been implicated in the leukocyte adhesion cascade. E-selectin supports the attachment and rolling of leukocytes on the endothelium while ICAM-1 is involved in the firm adhesion of the leukocyte to the endothelium.

Figure 2:
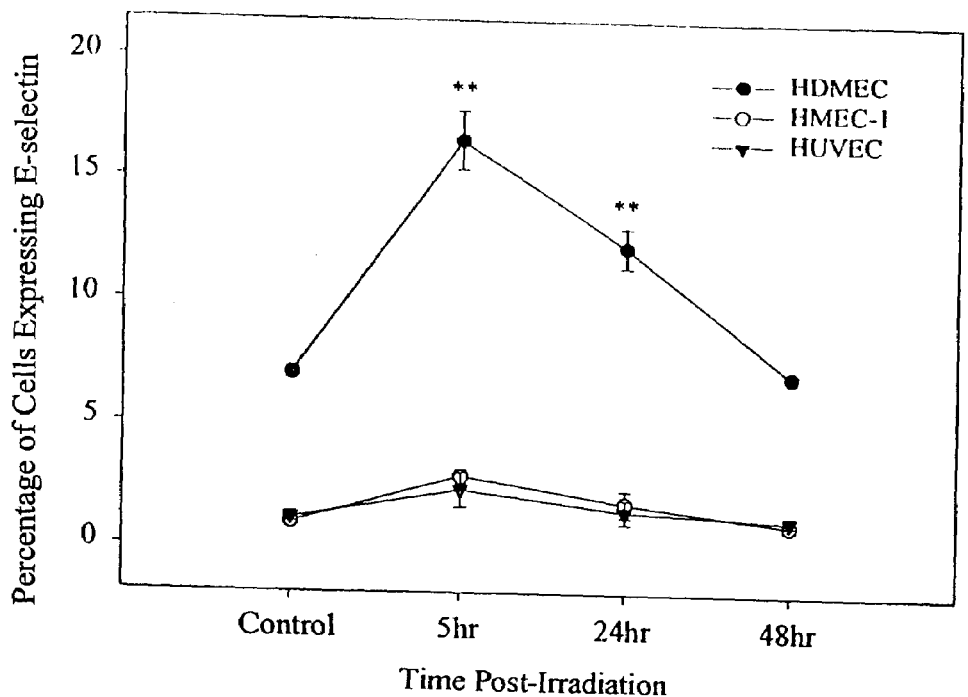
FIG. 2 shows the up-regulation of E-selectin on irradiated (10 Gy) endothelium.

Flow cytometric analysis revealed significant up-regulation of E-selectin on human microvascular endothelial cells 5 and 24 hr. post-irradiation (5–10 Gy single dose) but no up-regulation of E-selectin on human umbilical vein endothelial cells and HMEC-1 up to 48 hr post-irradiation (FIG. 2). Consistent with these findings, in vitro flow assays revealed an increase in the rolling and adhesion of a leukocytic cell line (HL60 cells) on post-irradiation human microvascular endothelial cells but no rolling of HL-60 cells on human umbilical vein endothelial cells and HMEC-1 monolayers post-irradiation. The increased rolling on post-irradiation human microvascular endothelial cells was reduced by more than 90% by pretreatment of the post-irradiation human microvascular endothelial cells with a mAb to E-selectin prior to introduction of the HL-60 cells (data not shown). Thus, it appears that E-selectin expression is up-regulated post-irradiation in some but not all in vitro endothelial cell models. Note that the literature is divided on the expression of E-selectin post-irradiation with one group reporting an increase (31–33) and others (21) reporting no expression of E-selectin post-irradiation.

Figure 3:
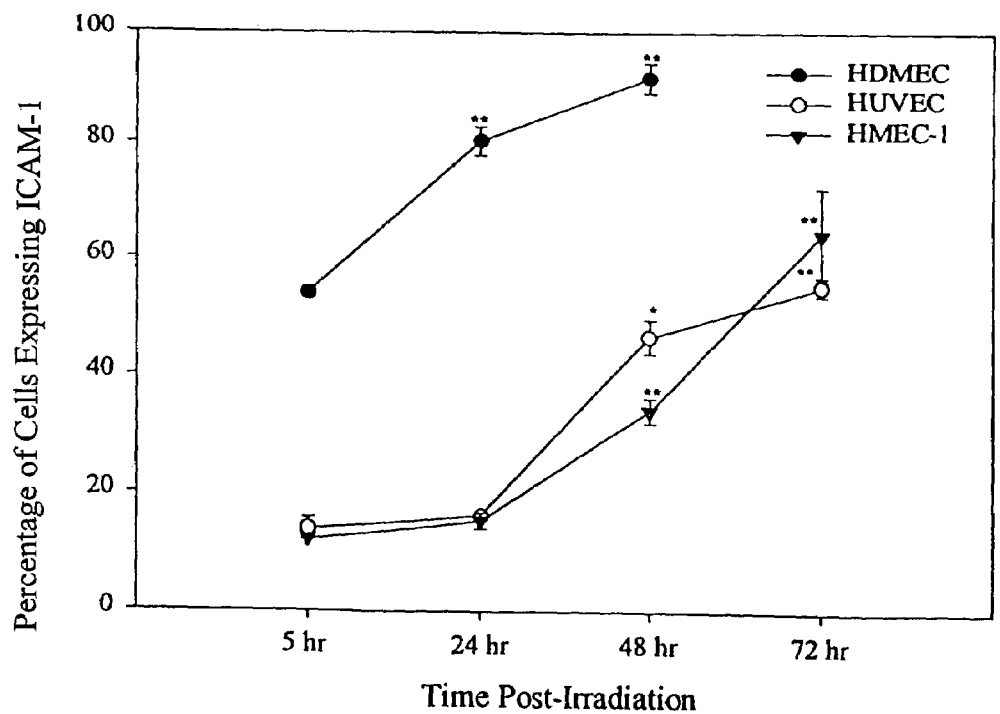
FIG. 3 shows the up-regulation of ICAM-1 on irradiated (10 Gy) endothelium.

In contrast to the variable results with E-selectin, ICAM-1 was significantly up-regulated in response to radiation (5–10 Gy single dose) on all three endothelial cell types tested (FIG. 3). These results are consistent with a variety of reports (35;36;53;53;58;59) showing up-regulation of ICAM-1 in response to irradiation. Thus, the response of ICAM-1 to irradiation appears to be "robust", i.e. occurring at several time points post-irradiation; occurring on all of the endothelial cells tested to date and being consistently reported as inducible post-IR.

EXAMPLE 12

Up-Regulation of Leukocyte-Endothelium Interaction in Irradiated Tissue In Vivo

Figure 4A:
FIG. 4 shows typical pictures of Rhodamine-6G labeled leukocytes in control (panel A) and 10 Gy irradiated (panel B) cerebral microvasculature.
Figure 4B:
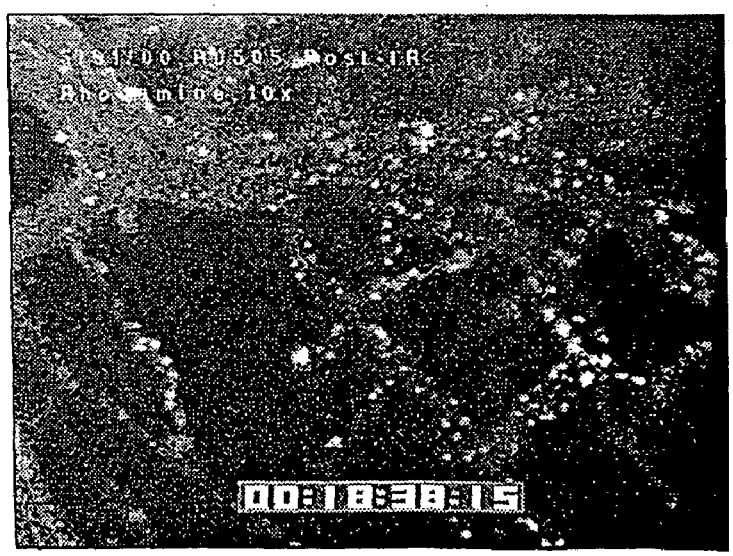
Figure 5:
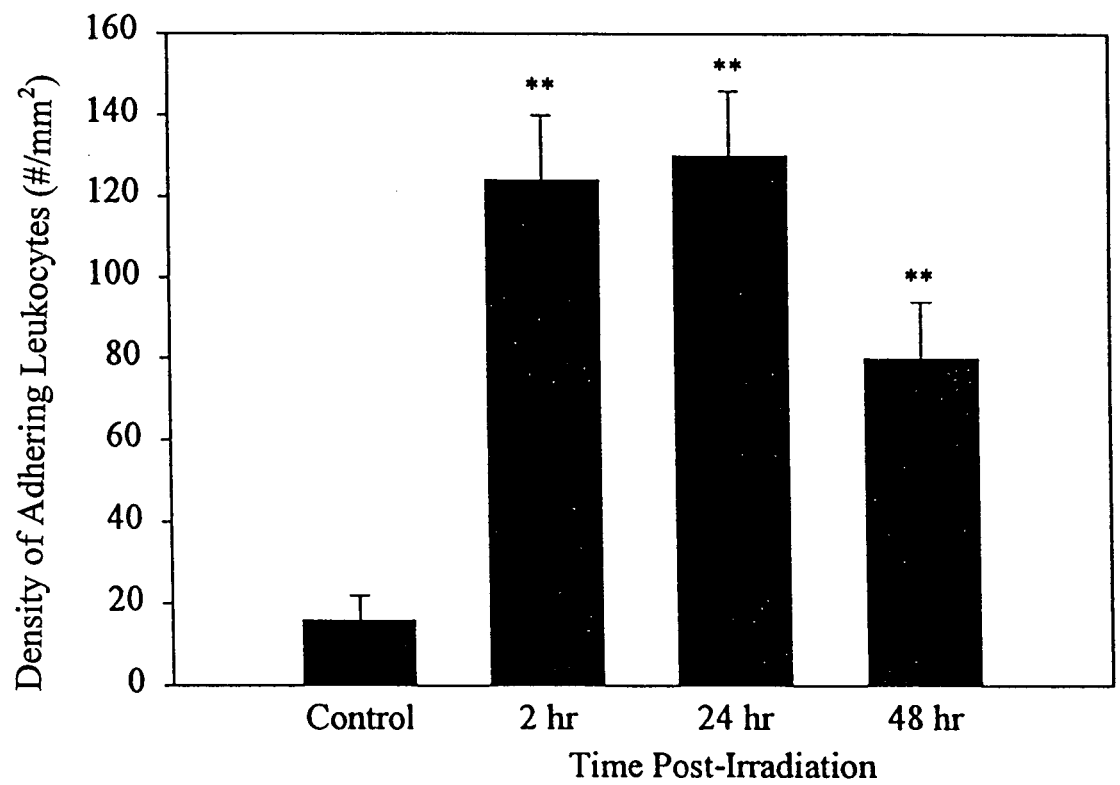
FIG. 5 shows the up-regulation of leukocyte adhesion in 10 Gy irradiated cerebral microvasculature.
Figure 6A:
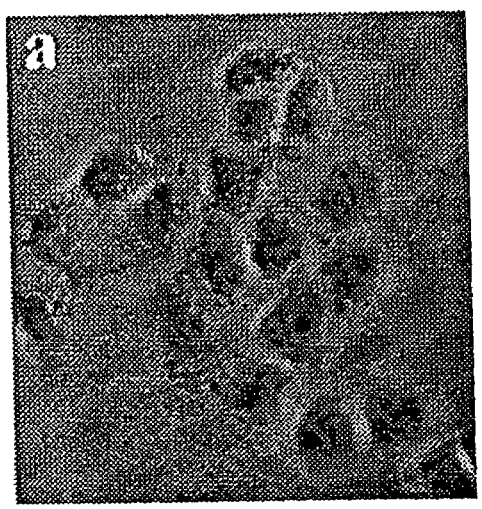
FIG. 6 shows adhesion of antibody bearing nanospheres to CHO-E.
Figure 6B:
Figure 6C:
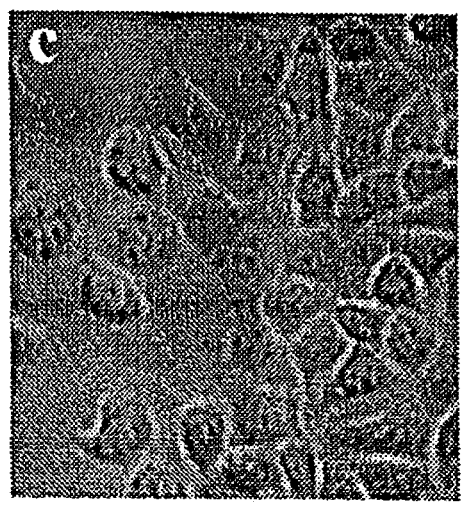
Figure 6D:
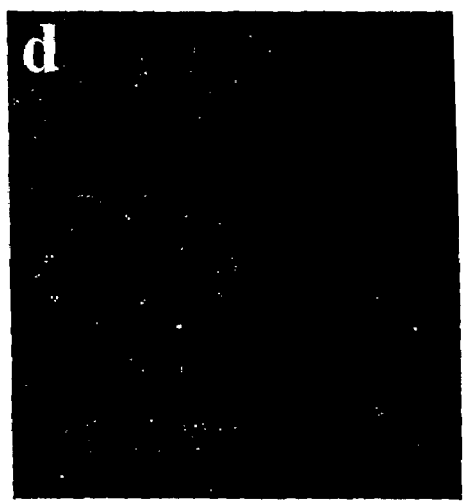
Figure 7:
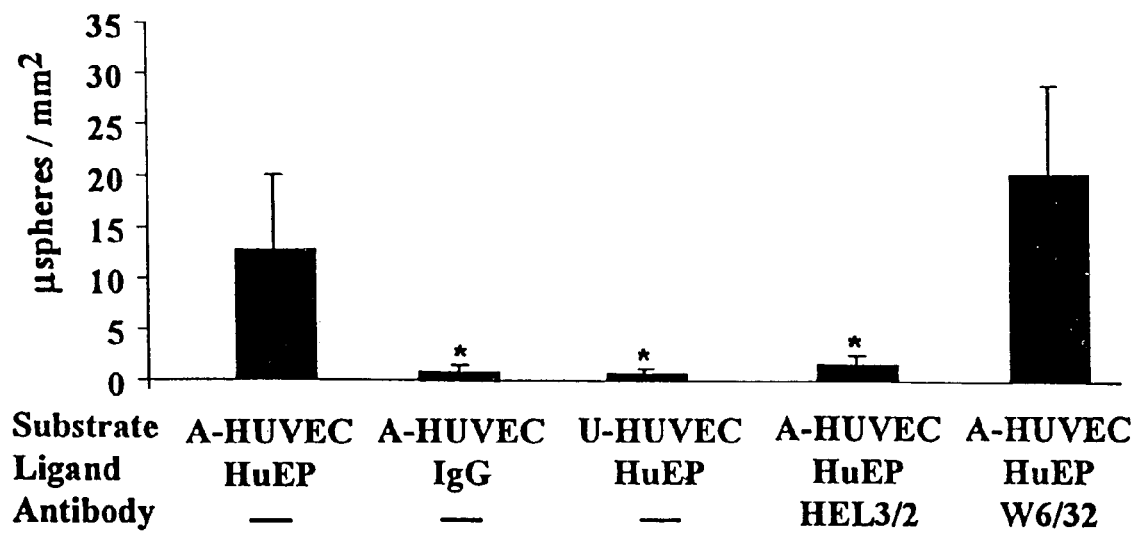
FIG. 7 shows the selective adhesion of biodegradeable microspheres to activated human umbilical vein endothelial cells.

A closed cranial window model was used to determine the effects of a single 10 Gy local dose of radiation on leukocyte-endothelial interactions in cerebral microvasculature in vivo. FIG. 4 shows digitized pictures of Rhodamine labeled leukocytes in the unirradiated (panel A) and 48 hours post-irradiated (panel B) cerebral microvasculature in the closed cranial window model. The results (n=6 animals) indicate that the number of adhering leukocytes was significantly elevated (~124 leukocytes/mm$^2$) at 2 hours post-irradiation and remained elevated up to 48 hours post-irradiation relative to control which stayed constant at ~16 leukocytes/mm$^2$ (FIG. 5) over the 2 hour to 48 hour time period studied. These results indicate that the up-regulation of leukocyte-endothelium interaction post-irradiation is present in vivo.

EXAMPLE 13

Making and Characterizing Ligand Coated Particles

Significant research has focused on the development of ligand coated particles for use in adhesion assays (6;13;16; 25;69). FIG. 6 (gives a typical result wherein 60 nm fluorescent (red) nanospheres were coated with either an antibody to E-selectin (mAb HuEP5C7.g2 (40)) or human IgG (negative control) and allowed to adhere to Chinese hamster ovary cells stably expressing E-selectin (CHO-E). Bright field microscopy (images (a) and (c)) shows the CHO-E monolayers.

Fluorescent microscopy (images (b) and (d)) reveals that the nanospheres coated with HuEP5C7.g2 (HuEP) exhibit significantly higher levels of adhesion than nanospheres coated with human IgG (image (b) compared to (d)). Note that the nanospheres are only bound to the surface where CHO-E cells are present (compare image (a) with (b)). This study was conducted with polystyrene particles which is not a very relevant drug delivery carrier. A more physiogically relevant drug delivery carrier could be made of a variety of materials including biodegradable polymers. Consequently, monoclonal antibody HuEP5C7.g2 was passively adsorbed onto particles made from the biodegradable polymer poly-($\epsilon$-caperlactone) (PCL) (16) and the adhesion of the resulting HuEP5C7.g2 PCL microspheres was studied.

The HuEP5C7.g2 poly-($\epsilon$-caperlactone) microspheres exhibit selective adhesion to activated HUVEC (A-HUVEC) relative to unactivated HUVEC (U-HUVEC) (FIG. 7) while poly-($\epsilon$-caperlactone) microspheres coated with human IgG do not. The adhesion of the HuEP5C7.g2 poly-($\epsilon$-caperlactone) microspheres was inhibited by pretreatment of the A-HUVEC with a monoclonal antibody to E-selectin (HEL3/2) but unaffected by pre-treatment with endothelial cell binding mAb W6/32. Although the adhesion appeared to be specific, the rate of attachment was quite low, occurring only under low shear (0.3 dynes/cm$^2$) and at a rate estimated to be <1% that exhibited by neutrophils. The low rate of attachment may be due to a low level of HuEP5C7.g2 coupled to the poly-($\epsilon$-caperlactone) microspheres via passive adsorption. Thus, particles made from a block copolymer of biotinylated poly(ethylene glycol) (PEG) with poly (lactic acid) (PLA) (9) can be used. Monoclonal antibody can be coupled to the particles via avidin-biotin chemistry allowing achievement of a high surface density of monoclonal antibody on the biodegradable particles (9). Note, the fact that the particles are made with poly(ethylene glycol) should enhance the circulation time of the particles.

EXAMPLE 14

Enhanced Adhesion of Antibody Bearing Microspheres to Irradiated Endothelial Cells In Vitro The interaction of antibody bearing polystyrene microspheres with irradiated endothelial cells was studied under static and shear flow conditions. The results indicate that under static conditions the number of adherent anti-ICAM-1 microspheres on 48 hr post-irradiated HUVEC was 4.9±1.8 (Mean±SEM) times that of control (P<0.01, N=3). Under shear flow conditions (1.5 dynes/cm$^2$) the number of adherent anti-ICAM-1 microspheres on irradiated HUVEC was 3.9±1.2 to 4.5±0.9 times (P<0.01, N=3 in each group) that of control HUVEC depending on the surface density of anti-ICAM-1 (see FIG. 8). The selectivity of this targeting mechanism may be further enhanced by optimizing particle size, antibody density, etc.

EXAMPLE 15

Enhanced Adhesion of Antibody Bearing Microspheres to Irradiated Tissue In Vivo

In a series of experiments (n=4 animals), the adhesion of polystyrene microspheres coated with a monoclonal antibody to ICAM-1 to irradiated (10 Gy single local dose of X-ray) cerebral microvasculature was investigated in a rat closed cranial window model.

Fluorescent 2 μm diameter microspheres coated with either rat anti-ICAM-1 antibody or IgG (negative control) were injected via tail vein into rat bearing closed cranial windows. Dual color fluorescent microscopy was used to quantify the level of adhesion of anti-ICAM-1 and IgG bearing microspheres to the cerebral venules before and after radiation.

Figure 8:
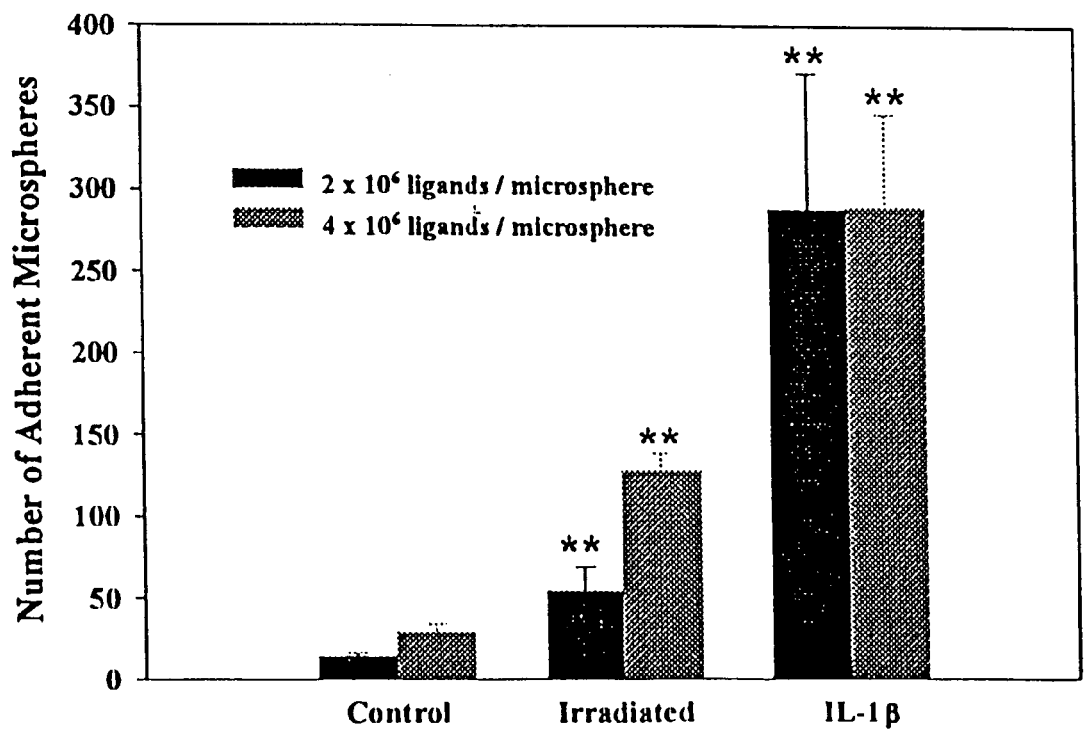
FIG. 8 shows the adhesion of anti-ICAM-1 microspheres to irradiated human umbilical vein endothelial cells under shear flow (1.5 dynes/cm2).
Figure 9A:
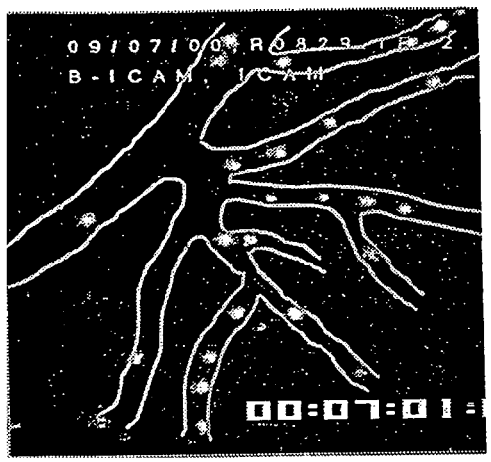
FIG. 9 shows the adhesion of anti-ICAM-1 (panel A) and IgG (panel B) microspheres to irradiated (10 Gy) cerebral microvasculature.
Figure 9B:
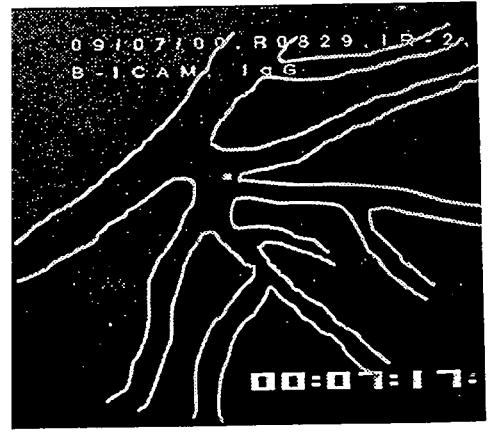
Figure 10:
FIG. 10 shows the adhesion of anti-ICAM-1 microspheres to control (before irradiation) cerebral microvasculature.
Figure 11:
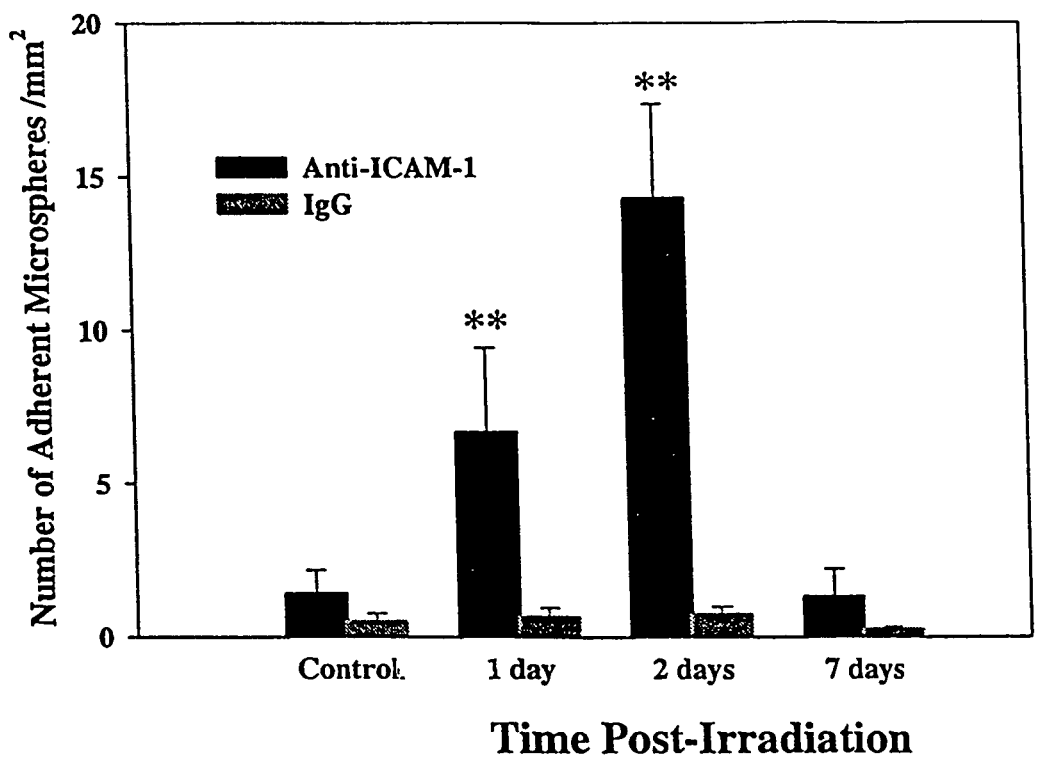
FIG. 11 shows the adhesion of anti-ICAM-1 and IgG microspheres to control and irradiated (10 Gy) cerebral microvasculature.
Figure 12:
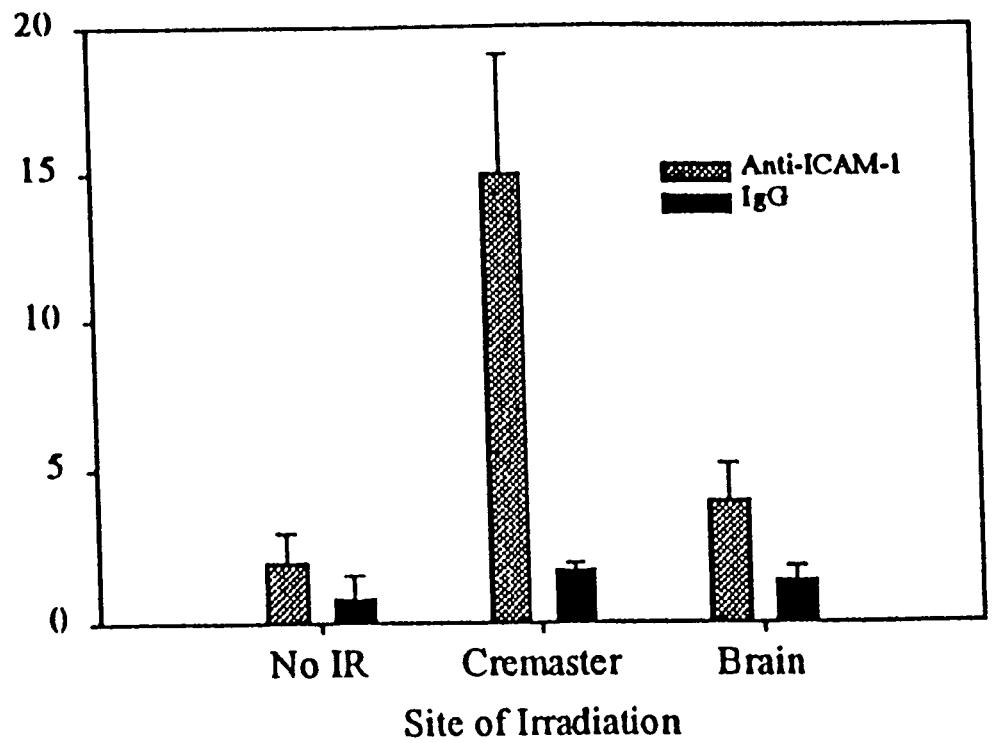
FIG. 12 shows the specificity of the targeting technique to the irradiated site as opposed to un-irradiated tissue. Adhesion of anti-ICAM-1 antibodies-bearing microspheres to the cremaster muscle of rat was shown. The data indicated that while irradiating the cremaster resulted in a significant increase in the adhesion of microspheres to the cremaster microvasculature, irradiating the brain did not significantly increase adhesion of microspheres to the cremaster microvasculature.

FIG. 9 shows that in the irradiated tissue a large number of anti-ICAM-1 coated microspheres adhere to the vessel wall (panel A), while very few IgG coated microspheres adhere to the walls of the same vessel (panel B). Microvascular outline as determined from reflected light microscopy has been digitally superimposed on FIGS. 9 and 10. There was also very little adhesion of anti-ICAM-1 coated microspheres to the same vessels before this area of the brain was irradiated (see FIG. 10). The compiled data from the 4 animals revealed that the adhesion of anti-ICAM-1 coated microspheres to the irradiated cerebral microvasculature is up to 25 times higher than control and reaches a peak 48 hours post-irradiation (see FIG. 11). The number of adhering antibody bearing microspheres to sham irradiated microvasculature did not significantly differ from control up to 7 days post-irradiation (data not shown). Note that the enhanced adhesion of antibody bearing microspheres to the irradiated tissue in vivo (FIG. 11) is much more pronounced compared to the adhesion of antibody bearing microspheres in vitro (FIG. 8). The presence of red cells in vivo, which have been shown to enhance the interaction of particles with the endothelium (52;54), is the reason for this higher rate of adhesion. This can be shown in vitro with a flow chamber system using microspheres suspended in media containing red blood cells.

In a series of control experiments (n=2) the adhesion of the anti-ICAM-1 and IgG bearing microspheres to the microvasculature of the cremaster muscle in animals which received local irradiation only to the brain was investigated to ascertain the preferential adhesion of anti-ICAM-1 coated microspheres to irradiated tissue. The results indicate that while the ratio of adherent anti-ICAM-1 coated microspheres was up to 25 times higher than that of IgG coated microspheres in the irradiated brain microvasculature, this ratio was only 2–3 times higher in the cremaster microvasculature. A basal level of anti-ICAM-1 coated microsphere adhesion to un-irradiated tissue is expected since a low level of ICAM-1 is constitutively expressed in all tissue under control conditions (27). The differential between the number of adherent particles to the brain microvasculature (irradiated tissue) vs. the cremaster microvasculature (un-irradiated tissue) would presumably be increased by directly injecting the drug carrying particles to arteries upstream of the irradiated tissue (e.g. the carotid artery for the brain).

The possibility exists that leukocytes may compete with the endothelium for binding to the drug carriers because ICAM-1 exists not only on endothelial cells but also on leukocytes (10). To investigate this possibility leukocytes were labeled in vivo with rhodamine-6G (fluorescent in red) and their interaction with anti-ICAM-1 coated microspheres (fluorescent in blue) was observed using dual fluorescent microscopy. By rapidly switching between red and blue fluorescent filters, one could then determine if any leukocyte -microsphere doublets were either circulating or attached to the vessel walls. In two experiments, no adhesive interactions between anti-ICAM-1 coated microspheres and leukocytes in vivo (no doublets) were observed.

These observations provide strong support for the specificity of targeting drug carriers to select tissue via the up-regulation of adhesion molecules expressed on endothelial cells in response to exposure to radiation.

The following references were cited herein:
1. Acker, et al., *Radiat. Res.* 149: 350–359, 1998.
2. Behrends, et al., *J. Invest. Dermatol.* 103: 726–730, 1994.
3. Bendas, et al., *Int J Pharm* 181: 79–93, 1999.
4. Bendas, et al., *Pharm Acta Helv* 73: 19–26, 1998.
5. Benoit, et al., *Int J Pharm* 184: 73–84, 1999.
6. Blackwell, et al., submitted 2000.
7. Bloemen, et al., *FEBS Letters* 357: 140–144, 1995.
8. Buell, et al., *Dig. Dis. Sci.* 34: 390–399, 1989.
9. Cannizzaro, et al., *Biotechnol Bioeng* 58: 529–535, 1998.
10. Carlos, et al., *Blood* 84: 2068–2101, 1994.
11. Chang, et al., *Biophys. J.* 76: 1280–1292, 1999.
12. Chiang, et al., *Int. J. Radiat.Biol.* 72: 45–53, 1997.
13. Crutchfield et al., *J. Leuk. Biol.* 67: 196–205, 2000.
14. Crutchfield, et al., *J. Leukoc. Biol.* 67: 196–205, 2000.
15. Diamond, et al., *Current Biology* 4: 506–517, 1994.
16. Dickerson, et al., submitted 2000.
17. Discher, et al., *Science* 284: 1143–1146, 1999.
18. Ebnet et al., *Histochem. Cell Biol.* 112: 1–23, 1999.
19. Eldor, et al., *Prostaglandins Leukotrienes Essential Fatty Acids* 36: 251–258, 1989.
20. Fajardo, et al., *Pathol. Annu.* 23: 297–230, 1988.
21. Gaugler, et al., *Int. J. Radiat. Biol.* 72: 201–209, 1997.
22. Gobbel, et al., *Radiat. Res.* 130: 236–240, 1992.
23. Goetz, et al., *Am. J. Pathol.* 149: 1661–1673, 1996.
24. Goetz, et al., *Int J Cancer* 65: 192–199, 1996.
25. Goetz, et al., *J. Cell Biol.* 137: 509–519, 1997.
26. Goldsmith, et al., *Thrombosis and Haemostasis* 55(3): 415–435, 1986.
27. Granger, et al., Physiology and Pathophysiology of Leukocyte Adhesion. New York, Oxford University Press. 1995.
28. Gref, et al., *Science* 263: 1600–1603, 1994.
29. Hahn, et al., *Cancer Res.* 52: 1750–1753, 1992.
30. Hallahan, et al., *Oncology (Huntingt)* 13: 71–77, 1999.
31. Hallahan et al., *Biochem. Biophys. Res. Commun.* 217: 784–795, 1995.
32. Hallahan, et al., *Cancer Res.* 56: 5150–5155, 1996.
33. Hallahan, et al., *Radiat.Res.* 147: 41–47, 1997.
34. Hallahan, et al., *Cancer Res.* 58: 5216–5220, 1998.
35. Hallahan, et al., *Proc. Natl. Acad. Sci. USA* 94: 6432–6437, 1997.
36. Hallahan, et al., *Cancer Res.* 57: 2096–2099, 1997.
37. Hallahan, et al., *Radiat. Res.* 152: 6–13, 1999.
38. Hammer, et al., *Biophys. J.* 62: 35–57, 1992.
39. Handschel, et al., *Int. J. Radiat. Oncol. Biol. Phys.* 45: 475–481, 1999.
40. He, et al., *J. Immunol.* 160: 1029–1035, 1998.
41. Heckmann, et al., *Exp.Cell Res.* 238: 148–154, 1998.
42. Hong, et al., *Int. J. Radiat. Oncol. Biol. Phys.* 33: 619–626, 1995.
43. Kansas, G., *Blood* 88: 3259–3287, 1996.
44. Kimura, et al., *Int. J. Radiat. Oncol. Biol. Phys.* 33: 627–633, 1995.
45. Kiser, et al., *Nature* 394: 459–62, 1998.
46. Kwock, et al., *Am. Rev. Respir. Dis.* 125: 95–99, 1982.
47. Kyrkanides, et al., *J. Neuroimmunol.* 95: 95–106, 1999.
48. Lok, et al., *J. Coll. Inter. Sci.* 91: 104–116, 1983.
49. Luscinskas, et al., *Annu. Rev. Med.* 47: 413–421, 1996.
50. Martin, et al., *Int. J. Radiat. Oncol. Biol. Phys.* 10: 1903–1906, 1984.
51. Matzner, et al., *J. Immunology* 140(8): 2681–2685, 1988.
52. Melder, et al., *Microvasc. Res.* 59: 316–322, 2000.
53. Molla, et al., *Int. J. Radiat. Oncol. Biol. Phys.* 45: 1011–1018, 1999.
54. Munn, et al., *Biophys. J.* 71: 466–478, 1996.
55. Needham, et al., *Cancer Res.* 60: 1197–1201, 2000.
56. Newton, et al., *J. Leukoc. Biol.* 61: 422–426, 1997.
57. Nguyen, et al., *Radiat. Res.* 2000.
58. Olschowka, et al., *Brain Behav. Immun.* 11: 273–285, 1997.
59. Panes, et al., *Gastroenterology* 108: 1761–1769, 1995.
60. Prabhakarpandian, et al., Submitted 2000.
61. Qin, et al., *Am. J. Clin. Oncol.* 20: 263–265, 1997.
62. Qin, et al., *Int. J. Radiat. Oncol. Biol. Phys.* 19: 1507–1510, 1990.
63. Quarmby, S et al *Arterioscler. Thromb. Vasc. Biol.* 19: 588–597, 1999.
64. Riccardi, et al., *Clin. Cancer Res.* 4: 69–73, 1998.
65. Rose, et al., *J. Surg. Oncol.* 49: 231–238, 1992.
66. Roth, N. M. and M. F. Kiani.. *Ann. Biomed. Eng.* 27: 42–47, 1999.
67. Roth, et al., *Radiat. Res.* 151: 270–277, 1999.
68. Russell, et al., *Cancer Treat. Rev.* 25: 365–376, 1999.
69. Shinde Patil, et al., submitted 2000.
70. Slatkin, et al., *Med. Phys.* 19: 1395–1400, 1992.
71. Spragg, et al., *Proc. Natl. Acad. Sci.* 94: 8795–8800, 1997.
72. Springer, T. A. *Cell* 76: 301–314, 1994.
73. Van Der et al., *Cytokine* 11: 831–838, 1999.
74. Villanueva, et al., *Circ.* 98: 1–5, 1998.
75. Witte, et al., *Cancer Res.* 49: 5066–5072, 1989.
76. Wu, et al., *Brit. J. Cancer* 69(5): 883–889, 1994.
77. Yuan, et al., Submitted 2000.
78. Zimmermann, et al., *Strahlenther. Onkol.* 174 Suppl 3: 62–65, 1998.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A method of treating a cancer in an individual in need of such treatment, comprising the steps of:
   irradiating a cancerous target tissue or organ in said individual; and
   administering to said individual a particle of biodegradable polymers or PEGylated copolymers comprising antibodies or antibody fragments that bind to ICAM-1 expressed on an endothelial cell of said irradiated tissue or organ and a pharmaceutical.

* * * * *